United States Patent [19]

Heidel

[11] Patent Number: 4,777,232

[45] Date of Patent: Oct. 11, 1988

[54] METHOD OF MANUFACTURING POLYSACCHARIDE GRAFT POLYMERS WHICH ABSORB WATER AND ARE CAPABLE OF SWELLING

[75] Inventor: Klaus Heidel, Marl, Fed. Rep. of Germany

[73] Assignee: Starchem GmbH, Krefeld, Fed. Rep. of Germany

[21] Appl. No.: 15,093

[22] Filed: Feb. 13, 1987

[30] Foreign Application Priority Data

Apr. 19, 1986 [DE] Fed. Rep. of Germany ....... 3613309

[51] Int. Cl.$^4$ ............................................ C08F 251/00
[52] U.S. Cl. .................................... 527/300; 527/312; 527/313; 527/314
[58] Field of Search ................ 527/300, 312, 313, 314

[56] References Cited

U.S. PATENT DOCUMENTS

| | | | |
|---|---|---|---|
| 4,340,706 | 7/1982 | Obayashi et al. | 525/383 |
| 4,417,025 | 11/1983 | Toba et al. | 527/314 |
| 4,690,996 | 9/1987 | Shih et al. | 527/314 |

*Primary Examiner*—John Kight
*Assistant Examiner*—Nathan M. Nutter
*Attorney, Agent, or Firm*—Oblon, Fisher, Spivak, McClelland & Maier

[57] ABSTRACT

The invention relates to a single-stage method of producing polysaccharide g FD-water/g polymers. Fine particulate graft polymers with very high water absorption capacity can be prepared by employing a nonionic lipophilic surface active agent and a nonionic hydrophilic surface active agent.

8 Claims, No Drawings

METHOD OF MANUFACTURING POLYSACCHARIDE GRAFT POLYMERS WHICH ABSORB WATER AND ARE CAPABLE OF SWELLING

BACKGROUND OF THE INVENTION

1. Field of the Invention

The invention relates to a method of manufacturing polysaccharide graft polymers which strongly absorb water and are thereby capable of swelling. The polymers are produced from a polysaccharide (as the grafting base) and unsaturated water-soluble monomers which contain carboxyl groups.

2. Description of the Background

Water absorbing polymers have numerous applications in the sanitary and hygiene areas, for example, as a water absorption medium in paper diapers and paper wipers, as tampons, hospital bedding, electrolyte thickeners in dry batteries, moisture conserving or water storing materials in agriculture, and as drying agents.

Suitable polymers are derivatized polysaccharides, generally grafted with water-soluble vinyl monomers. The polysaccharides employed include, for example, carboxymethyl-cellulose, hydrolyzed starch/acrylonitrile graft polymers, or acrylic acid/starch graft polymers. Other suitable water absorbing polymers include completely synthetic, weakly crosslinked polymers; e.g., crosslinked polyethylene oxide, or partially crosslinked polyacrylate salts. Of these polymers, carboxymethylcellulose and partially crosslinked polyethylene oxide have water absorption capacities, for fully deionized water ("FD"-water), which are only about 30 g per gram of polymer.

Partially saponified starch/acrylonitrile graft polymers, on the other hand, have high water absorption capacities, i.e., 300 to 500 g FD-water/g. These polymers can be prepared by grafting acrylonitrile on starch in aqueous suspension in the presence of Ce(IV) salts, with subsequent hydrolysis using aqueous NaOH or KOH, and possibly with purification by reprecipitation. This method requires the handling of acrylonitrile as a process material. Acrylonitrile is classified as hazardous. In addition, the monomers must be completely removed from the products by degassing which is particularly necessary if the products are to be used in the hygiene sector. Another consideration is that the hydrolysis of the nitrile groups is a technically difficult process, because it gives rise to highly viscous, water-swollen raw products having a doughy consistency and inferior water absorption capability. The water absorption capability can be improved only by tedious purification steps.

Accordingly, attempts have been made to synthesize water-absorptive graft polymers by direct grafting of water soluble monomers (e.g., acrylic acid and acrylamide) onto starch, in aqueous or alcoholic solution.

Japanese Pat. No. 40-43,408 describes a method of grafting unsaturated water-soluble monomers such as acrylic acid onto gelatinized starch, in aqueous solution in the presence of a water-soluble initiator system comprised of hydrogen peroxide and ascorbic acid. The method yields water soluble polymers with strong thickening action but low water absorption capacity (about 100 g FD-water/g).

It is also known, from Japanese Pat. No. 80-139,408, that graft polymerization of (meth)acrylic acid onto starch in aqueous solution, with initiation by water soluble peroxides, yields gel-like water-absorbing polymers with good water absorption capacity (>200 g FD-water/g). In order to achieve this result, it is necessary to bring about a weak crosslinking, by incorporating small amounts of di- or trifunctional compounds (e.g., glycerine diglycidyl ether, N,N'-methylenebisacrylamide, or 1,1,1-tris(hydroxymethyl)propane triacrylate.

The following difficulties are associated with polymerization of water soluble monomers in aqueous solution, with crosslinking, to produce particulate gels:

(1) The polymerization with crosslinking necessarily leads to a network of chains of low elasticity;

(2) The reaction products obtained are water-swollen gels, which are difficult to handle. The solid must be separated out by precipitation from the aqueous phase, yielding a clumped precipitate, which then must be dried and comminuted;

(3) Due to the swelling of the graft polymers, and high viscosity, it is not possible to intermix and stir the aqueous solutions, even at low solids contents of 10–20 wt. %. Therefore, it is not possible to carry out a controlled reaction in ordinary stirred apparatus;

(4) Using only water as a reaction medium, it is not possible to carry out effective graft polymerization of water soluble monomers onto starch, with formation of gel-containing graft polymers having the branched chain structure required for good water absorption capacity. Water soluble monomers such as acrylic acid or acrylamide polymerize in a solely water reaction medium with unavoidable side reactions leading to water soluble, non-grafted hompolymers, which have a thickening action but do not swell in water, and therefore detract from the water absorption capacity.

Measures to vary the degree of the graft polymerization can be employed in connection with the abovementioned aqueous solution polymerization technique. These include increasing the concentration of the grafting substrate, increasing the monomer concentration, and increasing the initiator concentration. However, the effects achievable by these measures are highly limited. When one increases the concentration of the grafting substrate, additional increases in the viscosity occur. Increasing the initiator concentration can lead to an uncontrollably high rate of polymerization, and low molecular weight.

The technique of water-in-oil suspension polymerization (inverse suspension polymerization) has been developed as an improved polymerization method for producing high molecular weight homo- and graft polymers in solid, fine particulate form.

This technique has proven to be very advantageous for producing graft polymers from polysaccharides such as starch, where the monomers used for the graft polymerization are water soluble. The success of the technique is attributable to the fact that the preconditions for effective graft polymerization are met (e.g., high concentrations of starch, monomers, and peroxide; and good stirrability of the suspensions). Inverse suspension polymerization for graft polymerization of water soluble monomers onto polysaccharides is described in German Pat. No. 28 40 010. The suspension polymerization is carried out semi-continuously. Starch, as the graft polymerization substrate, is suspended in petroleum ether containing a solvent-soluble, surface active agent such as sorbitan monooleate. An aqueous solution of the monomer which is prepared in a separate container is added, and the polymerization is begun by adding a radical initiator. The reaction is continued for 0.5 to 6 hr. The graft mixed polymer is isolated in the form of solid particles. The surface active agent is an essential feature of the method.

This technique has the following characteristics:

(1) The monomers are furnished in an aqueous solution prepared in a separate reaction vessel, along with a relatively high amount of a water soluble surface active agent which are then added to the organic phase. The surface active agent is regarded as necessary to attain homogeneous distribution of the aqueous phase in the organic phase. The so-called "semi-continuous" process requires an additional reaction vessel, which, when acrylic acid is being added as the monomer, must be equipped with a cooling apparatus to remove the heat of neutralization.

(2) Preferably, mixtures of ionic and nonionic surface active agents are used, in high amounts of from 0.5 to 12 wt. % based on the weight of the solvent.

Japanese Pat. No. 80-161,813 describes the production of a water-absorbing graft polymer by graft polymerization of acrylic acid onto a polysaccharide, in a gasoline-type hydrocarbon solvent, in the presence of an organophilic nonionic surface active agent and a water soluble initiator. For example, an aqueous phase comprising cornstarch, acrylic acid, NaOH, and sodium persulfate is dispersed in an organic phase comprised of n-hexane with 2 wt. % of sorbitan monostearate added, and polymerization is carried out for 6 hr at 60° C., to yield a gel-like graft polymer with a water absorption capacity of 600 g FD-water/g.

European No. A2 0 036 463 and German OS No. 33 31 644 and OS No. 35 07 775 describe methods of inverse suspension polymerization of carboxyl- or carboxylate group containing water soluble monomers in the presence of small amounts of a crosslinking agent, for producing strongly water-absorbing, gel-like polymers. In all the examples given, the polymerization is carried out by a semi-continuous method involving relatively high apparatus costs. The aqueous monomer solution is prepared by neutralization of acrylic acid with an aqueous alkali- or ammonium hydroxide solution, with cooling, in a separate reaction vessel, and this solution is then added in portions to the organic phase. These methods differ in the types of surface active agents used. The parameter known as the "HLB value" (Hydrophilic-lipophilic balance value) is used to characterize the surface active agent. Lipophilic surface active agents have HLB values of 0 to 10, and hydrophilic surface active agents have values of 10 to 20.

In the European No. A2 0 036 463, an oil-soluble surface active agent with relatively high HLB value of 8 to 12 is used, with sorbitan monolaurate preferred. High formation of gels and clumps occurs in the polymerization. The products are distinguished by high water absorption capacities, in some cases on the order of 1,000 g FD-water/g.

In German OS No. 33 31 644 and OS No. 35 07 775, the aqueous monomer solution is added portionwise to the organic phase, which is hot and which contains an oil-soluble surface active agent with low HLB-value. The water absorption capacities of the resulting polymers are approximately 450-750 g FD-water/g.

It can be concluded from these patent publications that when nonionic surface active agents with high HLB values (thus high water solubility) are used in semicontinuous suspension polymerization, the result is polymers with a large particle size and high water absorption capacity, and with a strong tendency to form gels. On the other hand, when nonionic surface active agents with low HLB values are used, the result is polymers with small particle size and low water absorption capacity, and a low tendency to form clumps.

There continues to be a need for a simplified method of producing graft polymers having a small particle size and high water absorption capacity but low water-solubility, using polysaccharides and carboxyl- or carboxylate containing vinyl monomers. The graft polymers should precipitate directly in the polymerization, as a powder with high water absorption capacity and low tendency to separate out on vessel walls or to form clumps.

SUMMARY OF THE INVENTION

Accordingly, one object of the present invention is to provide a method of manufacturing a graft polymer which is in particulate form and which swells substantially when exposed to water but has low water-solubility.

Another object of the invention is to provide a method of manufacturing a graft polymer in which there is a low tendency for the polymer to separate out on the walls of the vessel or to form clumps.

These objects and other objects of the invention which will become apparent from the following specification have been achieved by the present method for the manufacture of a graft polymer which is in particle form and which swells substantially when exposed to water, comprising polymerizing a dispersion comprising:

(i) an aliphatic hydrocarbon;
(ii) an aqueous solution of at least one water-soluble unsaturated monomer;
(iii) a polysaccharide; and
(iv) a combination of
  (a) a nonionic, water insoluble surface active agent which is at least partially soluble in the aliphatic hydrocarbon and which has an HLB value less than 10; and
  (b) a nonionic, water soluble, polyethyleneglycol-group-containing surface active agent with an HLB value greater than 10; wherein said polymerizing step is carried out as a single-stage batch radical polymerization.

DETAILED DESCRIPTION OF THE PREFERRED EMBODIMENTS

In contrast to the semi-continuous methods, in the present single-stage, batch inverse suspension polymerization, (meth)acrylic acid is neutralized by aqueous alkali in situ in the polymerization vessel, in the aqueous phase in the presence of the organic phase. According to the method of the present invention, one may add the alkali to the (meth)acrylic acid or vice versa.

The hydrocarbon solvent may have 6-12 C atoms. Hydrocarbons which may be used include aliphatic or alicyclic hydrocarbons such as cyclohexane, n-hexane, $C_8$ isoparaffins, or technical gasoline fractions such as nonaromatic gasoline, ligroin, mineral spirits, or solvent naphtha, with aromatic content $\leq 20\%$ and a boiling point in the range 50°-200° C.

The water soluble monomers are comprised of acrylic acid or methacrylic acid in the amount of 50-100 wt. %. In addition, up to 50 wt. % of water soluble comonomers may be used (e.g., (meth)acrylamide, the sodium salt of 2-acrylamido-2-methylpropanesulfonic acid, 2-methacryloylethanesulfonic acid, 2-hydroxyethyl (meth)acrylate, or N,N-dimethyl-aminoethyl (meth)acrylate or quaternary ammonium salts of the same.

Free carboxyl group containing monomers are partially neutralized in the polymerization vessel by adding aqueous solutions of NaOH, KOH, or NH$_4$OH in the amount of 50-95 mol %, preferably 65-80 mol %. If the degree of neutralization is greater than 50 mol %, there is a decrease in the water absorption capacity; if greater than 95 mol %, the graft polymers produced are water soluble rather than water-swellable. Preferably, alkali- or ammonium hydroxide solutions with concentrations of 15-30 wt. %. are employed.

After the water phase is prepared and is homogenized by stirring, the polysaccharide is added in granular form. Suitable polysaccharides include untreated starches from potatoes, corn, wheat, rice, or tapioca root; wax maize or high-amylose starch; or derivatives of the same, particularly starch ethers and starch esters. Also suitable are cellulose or cellulose derivatives.

The polysaccharide and water soluble monomer are used in weight ratios such that the graft polymers obtained comprise polysaccharide in the amount of 10-70 wt. % and vinyl polymer in the amount of 90-30 wt. %. Preferably, the graft polymer is comprised of polysaccharide in the amount of 30-50 wt. % and vinyl polymer in the amount of 70-50 wt. %.

The suspension agent combination has two components:

(1) at least one nonionic, water-insoluble surface active agent which is at least partially soluble in the aliphatic hydrocarbon and which has an HLB-value less than 10, preferably 5-10. Such surface active agents are preferably lipophilic sorbitan esters, e.g., sorbitan monolaurate (HBL-value=8.6) or sorbitan monopalmitate (HLB-value=6.7). Also highly preferred are polyethylene glycol (200) monooleate (HLB-value=7.0-8.3), polyethylene glycol (200) monolaurate (HLB-value=9.6), and polyethylene glycol (300 oleate (HLB-value=8.9). Less effective are sorbitan monooleate and -stearate (HLB-values 4.3 and 4.7, respectively). These surface active agents are used in concentrations of 1-30 wt. %, preferably 2-5 wt. % based on the weight of the water soluble monomer.

(2) At least one nonionic, water soluble surface active agent which contains polyethylene glycol (PEG) groups and has a HLB-value greater than 10, preferably 12-20. Such surface active agents are, for example, PEG ethers prepared from an aliphatic monohydric alcohol with 6-20 C atoms and a PEG with 3-30, preferably 4-20 ethylene oxide units. Also suitable are commercially available C$_{12}$ fatty alcohol PEG ethers with 7-19 ethylene oxide units (HLB-value 13-18). Particularly preferable are water soluble PEGs with molecular weights of 200-20,000, particularly 400-5,000. Also suitable are polyoxyethylene sorbitan fatty acid esters with HLB-value 10-20, such as polyoxyethylene sorbitan monolaurate (HLB-value 16.7), polyoxyethylene sorbitan monopalmitate (HLB-value 15.6), or polyoxyethylene sorbitan monooleate (HLB-value 15.0). These additives are used in concentrations of 1-10 wt. %, preferably 2-5 wt. % based on the weight of the water soluble monomer.

The graft polymerization is initiated by adding a water soluble, free radical supplying initiator, e.g., potassium persulfate, sodium persulfate, and/or ammonium persulfate, and heating to 40°-100° C. Other suitable initiators are hydroperoxides such as hydrogen peroxide, tert-butylperoxide, or cumene hydroperoxide. The peroxides are effective in the temperature range 50°-80° C. They may also be used together with water soluble reducing agents, such as ascorbic acid, and/or ferrous salts, sodium bisulfite, or sodium formaldehyde sulfoxylate (i.e., sodium hydroxymethane-sulfinate), as a redox pair, for initiation at low temperatures. The concentration of the peroxides should be 0.05-2 wt. %, preferably 0.2-0.5 wt. % based on the weight of the water soluble monomer. The reducing components may be used in concentrations of up to 0.2 wt. % based on said monomer.

During or after the polymerization, 0.01-2 wt. % of a completely or substantially water soluble crosslinking agent may be added. Preferable are compounds such as N,N'-methylenebisacrylamide, butanediol-1,4-di(meth)acrylate, dialkylmaleate, glycidyl methacrylate, allyl methacrylate, PEG (450) dimethacrylate, or ethylene glycol diglycidyl ether.

The graft polymerization may be carried out in ordinary reaction vessels suitable for batch reactions, equipped with a stirrer and possibly heating and cooling means. To start the graft polymerization, the starting mixture is heated to the reaction temperature under nitrogen, and the initiator is then added. Alternatively, it is possible to add the initiator to the polymerization mixture and start the polymerization by heating under inert gas. Both methods of initiation lead to high grade products.

Preferably the polymerization is carried out at 40°-80° C., particularly 55°-65° C. The reaction time is 0.5-6 hr. Because the graft polymerization is exothermic, the reaction mixture is cooled during the reaction. However, it is not necessary to carry out the polymerization under isothermal conditions.

The products precipitate out as fine granules or beads. They can be easily separated from the continuous phase, and can be dried to yield a powder, for example under vacuum or with the use of a fluidized bed dryer. The filtrate can be reused in the next polymerization, the water may be removed by azeotropic distillation.

"Fine particulate product" in the context of the present invention shall be understood to mean a product with particle size less than 2 mm.

There is very little formation of agglomerates and residues (residues attached to the sides of the vessel) of large dimensions.

The combination of a lipophilic and a hydrophilic surface active agent is an essential feature of the invention. It enables homogeneous, clump-free distribution of the starch granules in the aqueous monomer phase, and very good physical breakdown of the monomer phase along with the starch granules, whereby the monomer phase and starch granules are distributed as fine droplets in the organic phase.

Surprisingly, there is no gelatinization to form a highly coherent, highly viscous gel, which can only be stirred with difficulty, even though experience has shown that under other conditions when starch is heated in aqueous, salt-containing solutions or in the presence of aqueous alkali there is considerable gelatinization and agglutination. Thus, the inventive combination of surface active agents enables the graft polymerization to be carried out easily and without problems, in a batch mode.

During the polymerization there is no persistent or even temporary gel or clump formation. The amount of polymer which separates out onto the reactor walls and the stirrer is much less than in the case of graft polymerization carried out in the presence of only lipophilic surface active agents.

The advantages of the inventive method may be summarized as follows:

(1) The apparatus cost required for the single-stage, batch inverse suspension polymerization process is substantially less than that for the known semicontinuous processes, because it is not necessary to separately prepare the aqueous monomer solution and add it in measured amounts to the rest of the reaction mixture.

(2) The graft polymerization to form a fine particulate product is improved. The tendency to gelatinize and form clumps is reduced.

(3) The final product has excellent water absorption capacity.

Other features of the invention will become apparent in the course of the following descriptions of exemplary embodiments which are given for illustration of the invention and are not intended to be limiting thereof.

EXAMPLES

Comparison Example A

According to Japanese Pat. No. 80-161,813, 450 ml cyclohexane and 78 g acrylic acid were mixed, with stirring (400 rpm), in a 2-liter four-neck glass flask equipped with stirrer, reflux condenser, thermometer, dropping funnel, and nitrogen inlet. To neutralize the acrylic acid to the extent of 75%, 153 g 22.6% NaOH was added under cooling, followed by 11.3 g untreated cornstarch and 2.5 g sorbitan monostearate (Disponil ® SMS, applied by Henkel, of D-4000 Dusseldorf, FRG). The reaction mixture was stirred 30 min at 58° C. Then, 0.25 g ammonium persulfate dissolved in 10 ml water was added gradually, over 30 min. The polymerization proceeded with a temperature increase of 5° C. The graft polymer which formed was partly large particulate and partly clumps. The clumps were broken down to large beads, by intensive stirring. The polymerization was continued 3 hr at 60° C. The product was then separated from the organic phase by filtering, and then was dried at 50° C. for 24 hr, in an aspirator vacuum.

Yield: 106 g product (85% of theoretical). Of this,
87 g (82%) was bead and
19 g (18%) was residues of large dimensions which adhered to the walls of the vessel.

Comparison Example B

The procedure was the same as in Example A, above, except as follows: 43 g untreated cornstarch was added instead of 11.3 g. This resulted in a graft polymer comprising starch in the amount of 30 wt. %. The graft polymerization was initiated by adding 0.5 g ammonium persulfate dissolved in 10 ml water.

Yield: 143 g product (92% of theoretical). Of this,
136 g (96%) was bead and
7 g (5%) was residues of large dimensions which adhered to the walls of the vessel.

Comparison Example C

The procedure was the same as in Example A, above, except that 100 g untreated cornstarch was added. This resulted in a graft polymer comprising starch in the amount of 50 wt. %. The graft polymerization was initiated by adding 0.5 g ammonium persulfate dissolved in 10 ml water, and heating to 58° C. The reaction product was highly viscous, with the consistency of pudding. The stirrability was improved by adding 30 ml water and 50 ml cyclohexane. The polymerization was ended after 3 hr at 60° C.

Yield: 198 g product (93% of theoretical). Of this,
181 g (91%) was bead and
17 g (9%) was residues of large dimensions which adhered to the walls of the vessel.

EXAMPLE 1

The procedure was the same as in Example A, above, except as follows: Along with the 2.5 sorbitan monostearate, 2.5 g $C_{12}$ fatty alcohol PEG ether with 17 ethylene oxide units (Marlipal ® 1217, of Huels AG, of D-4370 Marl, FRG) was added as a second nonionic surface active agent. The polymerization proceeded with a temperature rise of 5° C., yielding a graft polymer in the form of fine particulate.

Yield: 123 g product (99% of theoretical). Of this,
121 g (98.4%) was fine particulate product, and
2 g (1.6%) was a gel of large particle size.

EXAMPLE 2

A graft polymer with a starch content of 30 wt. % was prepared as in Example B, above, except that the surface active agent combination of Example 1 was used.

Yield: 157 g product (99% of theoretical). Of this,
156 g (99.4%) was bead and
1 g (0.6%) was a gel material of large particle size, and residues of large dimensions which adhered to the walls of the vessel.

EXAMPLE 3

A graft polymer with a starch content of 50 wt. % was prepared as in Example C, above, except that the surface active agent combination of Example 1 was used.

Yield: 219 g product (100% of theoretical). Of this,
218 g (99.5%) was fine particulate fraction, and
1 g (0.5%) was gel material of large particle size.

Comparison Example D

The composition and amount of the reaction mixture were the same as in Comparison Example B, except that 2.5 g sorbitan monooleate (Span ® 20, supplied by Atlas, of Wilmington, Del.) was used instead of the sorbitan monostearate. The reaction was stirred at 60° C. for 30 min., under a stream of nitrogen. Then, a solution of 0.5 g ammonium persulfate in 10 ml water was added dropwise over 30 min., to initiate the polymerization. A bead-like graft polymer was produced, which was separated out by suction filtration and was then vacuum dried at 50° C. for 24 hr.

Yield: 151 g product (95% of theoretical). Of this,
120 g (79%) was bead and
31 g (21%) was gel material of large particle size.

EXAMPLE 4

The procedure was the same as in Example D, above, except that 3 g PEG with molecular weight 1,550 (Polydiol ® 1550, supplied by Huels AG) was used, in addition to the 2.5 g sorbitan monolaurate. After initiation of the polymerization, a fine particulate, bead-shaped product was formed.

Yield: 156 g product (97% of theoretical). Of this, 155 g (99.4%) was fine particulate, loose bead, and
1 g (0.6%) was gel material of large particle size.

EXAMPLE 5

The procedure was the same as in Example D, above, except that the polymerization was initiated by adding 1 g ammonium persulfate dissolved in 10 ml water.

Yield: 157 g product (97% of theoretical), with no gelatinous deposits.

EXAMPLE 6

Description of a Preferred Embodiment on an Industrial Scale 30 liter light gasoline (Exsol®, supplied by Esso AG) (boiling point range 80°–110° C.) was charged to a 60 liter polymerization autoclave comprised of $V_2A$ steel material, equipped with a blade stirrer, a thermometer, and filling nipples. To this the following were added slowly, with cooling of the vessel, and with stirring at 180 rpm: 5.07 kg anhydrous acrylic acid, followed by 9.36 kg 22.6% NaOH, in such a way that the interior temperature did not exceed 30° C. Then the following were added:

162 g sorbitan monolaurate,
81 g PEG (molecular weight 1,550),
2.8 g untreated cornstarch, and
32 g potassium peroxydisulfate.

Using a nitrogen atmosphere, the stirring speed was increased to 200 rpm and the interior temperature of the reactor was increased to 55° C. The graft polymerization began after 30 min, accompanied by an increase in the temperature. A recording device indicating the stirrer power showed only a slight increase in power consumption. This was evidence that the polymerization was proceeding smoothly. The polymerization was continued for another 3 hr. After cooling, the product, which precipitated out, was separated from the gasoline phase by suction filtration and was dried.

Yield: 9.56 kg product (95% of theoretical). Of this,
9.04 kg (94.6%) was bead and
0.52 kg (5.4%) was residues of large dimensions which adhered to the stirrer and the reactor.

EXAMPLE 7

450 ml light gasoline (boiling point in the range 80°–110° C.) was charged into a 2 liter 4-neck flask, and 63 g acrylic acid was stirred in. Then, the following were added under stirring:

115 g 22.6% NaOH,
19 g acrylamide,
43 g cornstarch,
2.5 g sorbitan monolaurate,
2 g PEG (molecular weight 1,550),
0.5 g PEG (molecular weight $6 \times 10^6$), and
0.5 g ammonium persulfate dissolved in 10 ml water.

The mixture was stirred 15 min at 400 rpm while being heated to 60° C. After 15 min, the polymerization began, with an increase in viscosity. However, there was no clumping. After 3 hr of polymerization, the polymer product was filtered out and dried at 50° C.

Yield: 154 g product. Of this,
153 g (99.4%) was fine particulate product, and
1 g (0.6%) was coarse residues of large dimensions which adhered to the walls of the vessel.

The water absorption capacity of the product was 902 g FD-water/g.

Alternately, the dewatering and further processing of the product may be accomplished by azeotropic distillation at 100° C., after the polymerization. This removed 71 g water (80%). The fine particulate product is then dried at 50° C. for 24 hr. The result is a product with a water absorption capacity of 530 g FD-water/g.

Comparison Example E

Illustration of polymerization of sodium acrylate in the presence of starch (starch comprising 50 wt. % of the polymer product) without using any suspension agent.

550 ml cyclohexane was charged into a 2 liter 4-neck flask. Then, the following were added, under stirring:

78 g acrylic acid,
144 g 22.6% NaOH, with cooling, and
100 g untreated cornstarch.

The temperature was increased to 60° C., under nitrogen, and maintained at 60° C. for 30 min giving a starting mixture of pudding-like consistency. Then, polymerization was initiated by adding 0.5 g potassium persulfate dissolved in 10 ml water. A large-particulate polymer formed, which was then filtered out, vacuum dried at 50° C., and comminuted.

Yield:
137 g (76%) ground powder, and
43 g (24%) clump-like residues of large dimensions which adhered to the stirrer and the walls of the reaction vessel.

EXAMPLE 8

The procedure was the same as in Example E, above, except that in addition, 2.5 g sorbitan monolaurate and 5 g PEG (molecular weight 1,550) were added. The polymerization yielded primarily a fine particulate product.

Yield: 211 g fine particulate product (97% of theoretical), with no gelatinous residues.

Comparison Example F 450 ml light gasoline (boiling point 80°–110° C.) was charged to a 2 liter 3-neck flask. The following were added under stirring:

78 g acrylic acid,
144 g 22.6% NaOH,
2.5 g sorbitan monolaurate,
43 g untreated cornstarch, and
0.5 g ammonium persulfate initiator, dissolved in 10 ml water.

The mixture was then heated to 55° C. under nitrogen. When polymerization proceeded, a clumped product formed. This was isolated, dried, and comminuted.

Comparison Example G

An attempt was made to adapt the semi-continuous graft polymerization process with separate preparation and addition of the monomer solution, which process employs a surface active agent combination comprised of a lipophilic agent (sorbitan monooleate) and a hydrophilic ionic agent (alkylbenzenesulfonate), as described in German Pat. No. 28 40 010, to the single-stage polymerization method according to the invention. In doing so, the sequence of additions set forth in German Pat. No. 29 40 010 was observed.

The following were added successively to 450 ml light gasoline (boiling point 80°–110° C.), with stirring:

43 g untreated cornstarch,
2.5 g sorbitan monooleate, 3 g sodium dodecylbenzenesulfonate (Marlon® A350, supplied by Huels AG),
144 g 22.6% NaOH, and
78 g acrylic acid (the latter added dropwise).

Then, 0.5 g ammonium persulfate, dissolved in 10 ml water, was added, and the reaction mixture was heated to 55° C. under a stream of nitrogen. When the polymerization proceeded, the product had the form of a clumped gelatinous material.

TABLE 1

| | Components | | | | | | | Polymer | | Water |
|---|---|---|---|---|---|---|---|---|---|---|
| Example No.: (%) | Acrylic Acid (g) | Degree of neutralization (%) | Acrylamide (g) | Starch (g) | Lipophilic Surface Active Agent (g) | Hydrophilic Surface Active Agent (g) | Course of the Polymerization | Fine Particulate (%) | Large Coarse Particulate (%) | Absorption Capacity (g/g) |
| A | 78 | 75 | | 11.3 | (1) 2.5 | — | Clumps form | 82 | 18 | 451 |
| B | 78 | 75 | | 43 | (1) 2.5 | — | Fine particulate product | 95 | 5 | 403 |
| C | 78 | 75 | | 100 | (1) 2.5 | — | Fine particulate product | 91 | 9 | 372 |
| D | 78 | 75 | | 43 | (2) 2.5 | — | Large particulate product | 79 | 21 | 475 |
| E | 78 | 70 | | 100 | — 2.5 | — | Large particulate product | 76 | 24 | 210 |
| F | 78 | 70 | | 43 | (3) 2.5 | — | Clumped product | | 100 | 479 |
| G | 78 | 70 | | 43 | (3) 2.5 | (4) 2.5 | Clumped product | | 100 | 756 |
| 1 | 78 | 75 | | 11.3 | (1) 2.5 | (5) 2.5 | Fine particulate product | 98.4 | 1.6 | 488 |
| 2 | 78 | 75 | | 43 | (1) 2.5 | (5) 2.5 | Fine particulate product | 99.4 | 0.6 | 408 |
| 3 | 78 | 75 | | 100 | (1) 2.5 | (5) 2.5 | Fine particulate product | 99.5 | 0.5 | 388 |
| 4 | 78 | 75 | | 43 | (2) 2.5 | (6) 2.5 | Fine particulate product | 99.4 | 0.6 | 756 |
| 5 | 78 | 75 | | 43 | (2) 2.5 | (6) 2.5 | Fine particulate product | 100 | 0 | 826 |
| 6 | 5070 | 75 | | 2800 | (2) 162 | (6) 81 | Fine particulate product | 94.6 | 5.4 | 825 |
| 7 | 63 | 75 | 19 | 43 | (2) 2.5 | (6) 2.5 | Fine particulate product | 99.3 | 0.6 | 902 |
| 8 | 78 | 70 | — | 100 | (2) 2.5 | (6) 5.0 | Fine particulate product | 100 | — | 530 |

(1) Sorbitan monostearate
(2) Sorbitan monolaurate
(3) Sorbitan monooleate
(4) Sodium dodecylbenzene sulfonate
(5) $C_{12}$—fatty alcohol PEG ether
(6) PEG with molecular weight 1.550

If the sequence of addition of the components was changed such that the acrylic acid was added first and then the NaOH was added, the result was also unsatisfactory, with gelatinous clumps again being formed.

Thus, the combination of surface active agents used in German Pat. No. 28 40 010 leads to a poor result in the case of in situ preparation of the aqueous monomer solution, and thus that combination cannot be employed successfully with the inventive method.

The results of Examples 1 to 8 and Comparison Examples A to G are summarized in Table 1. The data given for the water absorption capacity (measured by the centrifuge method) of the graft polymers were determined as follows. Approximately 50 mg of the dried product (G1) with particle size 0–200 micron, obtained by screening, was subjected to swelling by 80 ml FD-water in a 100 ml centrifuge tube, under mild agitation by a magnetic stirrer. The gel portion was then separated out by centrifuging at 5,000 rpm for 30 min. Adhering sol was removed by swabbing with cellulose, and the remainder was weighed (G2). The water absorption capacity, in g FD-water/g product, was then calculated as $(G2-G1)/G1$.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method of manufacturing a graft polymer which is in particle form and which swells substantially when exposed to water, comprising
polymerizing a dispersion comprising:
   (i) an aliphatic hydrocarbon;
   (ii) an aqueous solution of at least one water-soluble unsaturated monomer;
   (iii) a polysaccharide; and
   (iv) a combination of (a) a nonionic, water-insoluble surface active agent which is at least partially soluble in said aliphatic hydrocarbon and which has an HLB value less than 10; and (b) a nonionic, water-soluble polyethylene-glycol-group-containing surface active agent with an HLB value greater than 10;
wherein said polymerizing step is carried out as a single-stage batch radical polymerization.

2. The method of claim 1, wherein said polymerizing is carried out at temperatures between about 40°–100° C.

3. The method of claim 1, wherein said polymerizing is carried out in the presence of a surface active agent with an HLB value of 5-10 and a polyethylene-glycol-group-containing surface active agent with an HLB value of 12-20.

4. The method of claim 1, wherein said graft polymer comprises 10-70 wt. % polysaccharide and 90-30 wt. % unsaturated monomer.

5. The method of claim 4, wherein said graft polymer comprises 30-50 wt. % of said polysaccharide and 70-50 wt. % of said unsaturated monomer.

6. The method of claim 1, wherein said polysaccharide is starch.

7. The method of claim 1, wherein said water soluble unsaturated monomer is (meth)acrylic acid, and wherein prior to said polymerizing, said methacrylic acid is neutralized to the extent of 50-95% in the presence of an aliphatic hydrocarbon.

8. The method of claim 1, wherein said water insoluble surface active agent is a sorbitan ester and said water soluble surface active agent is an alkoxyethylate or polyethylene glycol.

* * * * *